US009539030B2

(12) United States Patent
Olsen et al.

(10) Patent No.: US 9,539,030 B2
(45) Date of Patent: Jan. 10, 2017

(54) MULTI-AXIS ADJUSTABLE SPLINT

(71) Applicant: ApMed LLC, Osage Beach, MO (US)

(72) Inventors: Ron A. Olsen, Queen Creek, AZ (US); Robert Horneff, Vancouver, WA (US)

(73) Assignee: APMED LLC MO (US)

( * ) Notice: Subject to any disclaimer, the term of this patent is extended or adjusted under 35 U.S.C. 154(b) by 136 days.

(21) Appl. No.: 14/247,239

(22) Filed: Apr. 7, 2014

(65) Prior Publication Data

US 2014/0303622 A1   Oct. 9, 2014

Related U.S. Application Data

(60) Provisional application No. 61/809,172, filed on Apr. 5, 2013.

(51) Int. Cl.
| | | |
|---|---|---|
| A61B 17/17 | (2006.01) | |
| A61B 17/64 | (2006.01) | |
| A61F 5/058 | (2006.01) | |

(52) U.S. Cl.
CPC ......... *A61B 17/6466* (2013.01); *A61B 17/171* (2013.01); *A61B 17/6475* (2013.01); *A61F 5/058* (2013.01); *A61F 5/0585* (2013.01)

(58) Field of Classification Search
CPC ......... A61B 17/68; A61B 17/60; A61B 17/64; A61B 17/6408; A61B 17/6416; A61B 17/6466; A61B 17/6475; A61B 17/171; A61B 17/6458; A61B 17/66; A61B 17/6441; A61B 17/6483; A61F 5/04; A61F 5/058; A61F 5/0585

USPC ......................................................... 606/59
See application file for complete search history.

(56) References Cited

U.S. PATENT DOCUMENTS

| | | | | |
|---|---|---|---|---|
| 4,483,334 | A * | 11/1984 | Murray ........................ | 606/59 |
| 4,620,533 | A * | 11/1986 | Mears ................. | A61B 17/645 |
| | | | | 606/54 |
| 5,746,741 | A * | 5/1998 | Kraus et al. .................... | 606/56 |
| 6,217,577 | B1 * | 4/2001 | Hofmann ....................... | 606/57 |
| 7,507,240 | B2 | 3/2009 | Olsen | |
| 7,575,575 | B2 | 8/2009 | Olsen | |
| 7,588,571 | B2 | 9/2009 | Olsen | |
| 2006/0229605 | A1 * | 10/2006 | Olsen ............................. | 606/54 |
| 2007/0123860 | A1 * | 5/2007 | Francis et al. ................. | 606/61 |
| 2007/0233061 | A1 * | 10/2007 | Lehmann et al. ............. | 606/59 |
| 2009/0118733 | A1 * | 5/2009 | Orsak et al. .................... | 606/60 |
| 2012/0209266 | A1 * | 8/2012 | Ottoboni et al. .............. | 606/59 |
| 2014/0276815 | A1 * | 9/2014 | Riccione ........................ | 606/54 |
| 2014/0371801 | A1 * | 12/2014 | Dall et al. .................. | 606/86 R |

* cited by examiner

*Primary Examiner* — Jacqueline Johanas
(74) *Attorney, Agent, or Firm* — Kunzler Law Group, PC (57) ABSTRACT

A multi-axis adjustable splint for treating the fracture of bones includes a rail body that has a longitudinal axis. The splint further includes a fixed clamp assembly coupled to the rail body for securing at least one first bone screw in a first desired orientation. The fixed clamp assembly is translationally fixed relative to the rail body. The adjustable splint further includes a movable clamp assembly movably coupled to the rail body for securing at least one second bone screw in a second desired orientation. The movable clamp assembly is translatable along the longitudinal axis of the rail body. Both the fixed clamp assembly and the movable clamp assembly are each independently adjustable about three axes of rotation relative to the rail body.

11 Claims, 9 Drawing Sheets

MULTI-AXIS ADJUSTABLE SPLINT

CROSS-REFERENCES TO RELATED APPLICATION

This application claims the benefit of U.S. Provisional Patent Application No. 61/809,172, filed Apr. 5, 2013, which is incorporated herein by reference.

FIELD

The subject matter of the present disclosure relates generally to adjustable splints for osteosynthesis. More specifically, this application relates to an adjustable splint device useful for treating the fracture of bones, e.g., ankle, wrist and facial bones.

BACKGROUND

When fractured bones are properly splinted, they often are able to heal in an appropriate manner thereby simulating the shape and function of the previously uninjured, natural bone. Bone fixation devices are often employed in the treatment of fractures of small bones such as bones in the foot, hand or maxiofacial regions, but also with a variety of different bone types. Such fixation devices are often known as minisplint devices, particularly when used in the treatment of small bones.

Typical minisplint devices feature a longitudinal support body and a pair of clamps mounted on the longitudinal support body. A clamp can be moved along the body through the use of an adjustable lead screw extending through the support body. Bone screws that are transverse to the longitudinal body connect to the clamps and secure the minisplint to the bone. By adjusting the lead screw, the position of the clamps can be moved with respect to the longitudinal support, thereby adjusting the size and configuration of the splint and the location of the transverse bone screws.

One limitation to typical adjustable minisplint devices is that the clamp connected to the longitudinal support is only moveable in an axial, linear direction with respect to the longitudinal support. The bone screws are also limited in their orientation. This dynamic limits the practitioner's options when attempting to set one or more bones using such minisplint devices.

Another limitation with typical minisplint devices relates to the positioning of one longitudinal support with respect to another longitudinal support. Such positioning typically results in limited movement, again reducing treatment options.

Yet another limitation associated with previous minisplint devices is that the lead screw used to provide adjustment of the bone clamps is retained in the longitudinal support body through the use of complicated multi-part systems that require a number of different parts to be added to the device assembly.

Another disadvantage of typical devices is that the lead screw of the devices projects outwardly from the elongated body, thereby exposing the lead screw to being inadvertently turned.

SUMMARY

From the foregoing discussion, it should be apparent that a need exists for an adjustable splint apparatus and system that overcome the limitations of conventional splint assemblies. Beneficially, such an apparatus and system would provide a flexible and convenient manner to treat the fracture of bones.

The subject matter of the present application has been developed in response to the present state of the art, and in particular, in response to the problems and needs in the art that have not yet been fully solved by currently available splint assemblies. Accordingly, the present disclosure has been developed to provide an adjustable splint that overcomes many or all of the above-discussed shortcomings in the art.

The present disclosure relates to one embodiment of an adjustable splint for treating the fracture of bones. The adjustable splint includes a rail body that has a longitudinal axis. The splint further includes a fixed clamp assembly coupled to the rail body for securing at least one first bone screw in a first desired orientation. The fixed clamp assembly is translationally fixed relative to the rail body. The adjustable splint further includes a movable clamp assembly movably coupled to the rail body for securing at least one second bone screw in a second desired orientation. The movable clamp assembly is translatable along the longitudinal axis of the rail body. Both the fixed clamp assembly and the movable clamp assembly are each independently adjustable about three axes of rotation relative to the rail body.

In one embodiment, the fixed clamp assembly and the movable clamp assembly each include a carriage portion coupled to the rail body, a joint mechanism connected to the carriage portion, and a rotatable portion that is pivotally engaged to the joint mechanism. The rotatable portion may include a top clamp member and a bottom clamp member that clamp around the first or second bone screws. Further, the rotatable portion may include a spherical collar rotatably supported within a socket. In such an embodiment, the spherical collar may be independently adjustable relative to the clamp assembly (fixed or movable). In one implementation, the rotatable portion includes two spherical collars rotatably supported within two sockets.

In one embodiment, the adjustable splint includes a single clamp nut engaged with the clamp assembly. The single clamp nut is tightenable to secure both the position of the spherical collar within the socket and the position of the rotatable portion about the joint mechanism. In one embodiment, the joint mechanism includes ball-joint bolt assembly that engages the rotatable portion. The rail body may include a lead bolt that extends longitudinally within the rail body. The lead bolt may be threadably engaged with the movable clamp assembly so that rotation of the lead bolt within the rail body causes the movable clamp assembly to move along the longitudinal axis of the rail body. The adjustable splint may further include an actuator screw cap that rotatably locks the position of the lead bolt in order to secure the translational position of the movable clamp assembly.

The adjustable splint may further include a second rail body coupled to the first rail body. At least one of a second fixed clamp assembly and a second movable clamp assembly may be coupled to the second rail body. In one embodiment, the first rail body and the second rail body extend in non-parallel directions. In another embodiment, the fixed clamp assembly and the movable clamp assembly of the first rail body extend from the first rail body in a first direction and the at least one of the second fixed clamp assembly and the second movable clamp assembly extend from the second rail body in a second direction, wherein the first direction and the second direction are substantially opposite directions. In one embodiment, the adjustable splint may include multiple fixed clamp assemblies and/or multiple movable clamp assemblies.

The present disclosure also relates to another embodiment of an adjustable splint for treating the fracture of bones. The adjustable splint may include a rail body that has a lead bolt extending longitudinally within the rail body. The adjustable splint further includes a fixed clamp assembly that has a carriage portion translational fixed to the rail body, a joint mechanism connected to the carriage portion, and a rotatable portion that is pivotally engaged to the joint mechanism. The rotatable portion includes a top clamp member and a bottom clamp member that clamp around a first bone screw to securing the first bone screw in a first desired orientation.

The adjustable splint further includes a movable clamp assembly that has a carriage portion mounted to the lead bolt so as to be movable along the length of the rail body, a joint mechanism connected to the carriage portion, and a rotatable portion that is pivotally engaged to the joint mechanism. The rotatable portion includes a top clamp member and a bottom clamp member that clamp around a second bone screw to securing the second bone screw in a second desired orientation. The fixed clamp assembly and the movable clamp assembly are each independently adjustable about three axes of rotation relative to the rail body. In one embodiment, each rotatable portion has a spherical collar rotatably supported within a socket, wherein the spherical collar is independently adjustable relative to the clamp assembly. In such an embodiment, the fixed clamp assembly and the movable clamp assembly may each include a single clamp nut that is tightenable to secure both the position of the spherical collar within the socket and the position of the rotatable portion about the joint mechanism. In one embodiment, each rotatable portion includes two spherical collars rotatably supported within two sockets, wherein the spherical collars are independently adjustable relative to each other. Still further, the adjustable splint may include a second rail body coupled to the first rail body and at least one of a second fixed clamp assembly and a second movable clamp assembly coupled to the second rail body.

The present disclosure also relates to an adjustable drilling jig for guiding drill bits for treating the fracture of bones. The adjustable drilling jig includes a rail body having a longitudinal axis and a fixed clamp assembly coupled to the rail body for securing at least one first drill jig in a first desired orientation. The fixed clamp assembly is translationally fixed relative to the rail body. The adjustable drilling jig further includes a movable clamp assembly movably coupled to the rail body for securing at least one drill jig in a second desired orientation, with the movable clamp assembly being translatable along the longitudinal axis of the rail body. In one embodiment, the fixed clamp assembly and the movable clamp assembly are each independently adjustable about three axes of rotation relative to the rail body.

Reference throughout this specification to features, advantages, or similar language does not imply that all of the features and advantages that may be realized with the present disclosure should be or are in any single embodiment of the invention. Rather, language referring to the features and advantages is understood to mean that a specific feature, advantage, or characteristic described in connection with an embodiment is included in at least one embodiment of the subject matter disclosed herein. Thus, discussion of the features and advantages, and similar language, throughout this specification may, but do not necessarily, refer to the same embodiment.

Furthermore, the described features, advantages, and characteristics of the disclosure may be combined in any suitable manner in one or more embodiments. One skilled in the relevant art will recognize that the subject matter of the present application may be practiced without one or more of the specific features or advantages of a particular embodiment. In other instances, additional features and advantages may be recognized in certain embodiments that may not be present in all embodiments of the disclosure. Further, in some instances, well-known structures, materials, or operations are not shown or described in detail to avoid obscuring aspects of the subject matter of the present disclosure. These features and advantages of the present disclosure will become more fully apparent from the following description and appended claims, or may be learned by the practice of the disclosure as set forth hereinafter.

BRIEF DESCRIPTION OF THE DRAWINGS

In order that the advantages of the disclosure will be readily understood, a more particular description of the disclosure briefly described above will be rendered by reference to specific embodiments that are illustrated in the appended drawings. Understanding that these drawings depict only typical embodiments of the disclosure and are not therefore to be considered to be limiting of its scope, the subject matter of the present application will be described and explained with additional specificity and detail through the use of the accompanying drawings, in which.

DETAILED DESCRIPTION

Reference throughout this specification to "one embodiment," "an embodiment," or similar language means that a particular feature, structure, or characteristic described in connection with the embodiment is included in at least one embodiment of the present disclosure. Thus, appearances of the phrases "in one embodiment," "in an embodiment," and similar language throughout this specification may, but do not necessarily, all refer to the same embodiment. Similarly, the use of the term "implementation" means an implementation having a particular feature, structure, or characteristic described in connection with one or more embodiments of the present disclosure, however, absent an express correlation to indicate otherwise, an implementation may be associated with one or more embodiments.

In the following description, numerous specific details are provided. One skilled in the relevant art will recognize, however, that the subject matter of the present application may be practiced without one or more of the specific details, or with other methods, components, materials, and so forth. In other instances, well-known structures, materials, or operations are not shown or described in detail to avoid obscuring aspects of the disclosure.

Illustrated in FIGS. 1-10 are several representative embodiments of a multi-axis adjustable splint for treating the fracture of bones, which embodiments also include one or more methods of treating the fracture of bones. As described herein, the multi-axis adjustable splint provides several significant advantages and benefits over other splints and methods for treating the fracture of bones. However, the recited advantages are not meant to be limiting in any way, as one skilled in the art will appreciate that other advantages may also be realized upon practicing the present disclosure.

Figure 1:
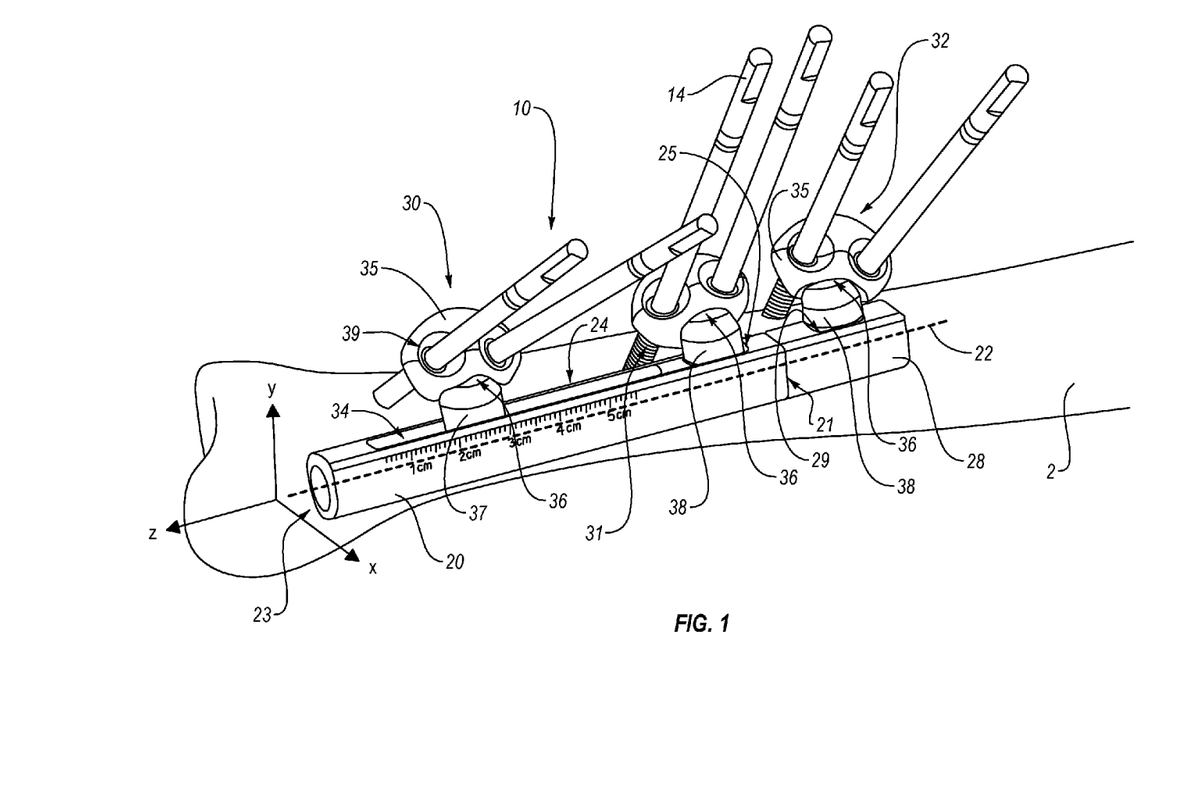
FIG. 1 is a perspective back-side view of a multi-axis adjustable splint attached to the bone of a patient, in accordance with an embodiment of the present disclosure.
Figure 2:
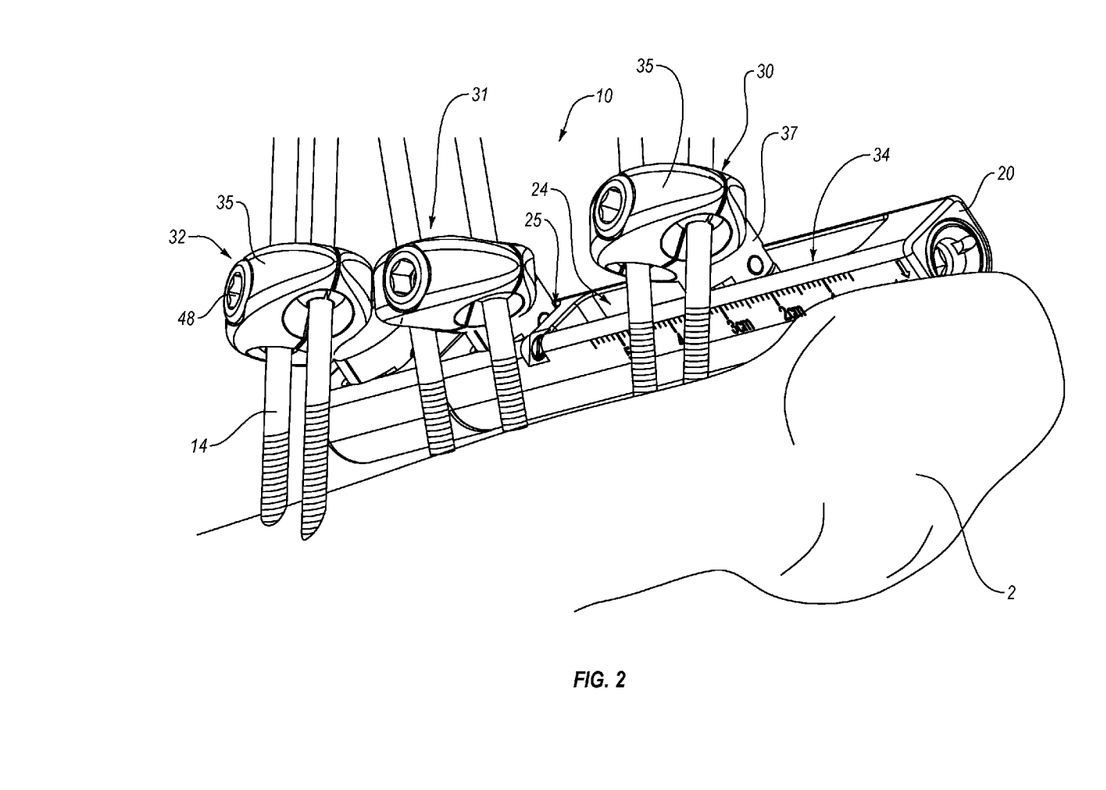
FIG. 2 is a perspective front-side view of the multi-axis adjustable splint of FIG. 1.

FIGS. 1-2 show a representative embodiment of a multi-axis adjustable splint 10 attached to the bone 2 of a patient. The splint 10 includes a rail body 20, a movable clamp assembly 30, one or more fixed clamp assemblies 31, 32 and a translation mechanism 34 for moving the movable clamp assembly relative to the rail body and the fixed clamp assembly or assemblies. In the illustrated embodiment, the multi-axis adjustable splint 10 includes one movable clamp assembly 30 and two fixed clamp assemblies 31, 32.

Each clamp assembly, whether movable or fixed, includes a rotatable portion 35 supported on a joint mechanism 36 which allows the rotatable portion to be independently rotated or pivoted about all three axes relative to a pivot point centered within the joint mechanism of that clamp assembly. As better seen in FIG. 2, for instance, all three clamp assemblies 30, 31, 32 have been tilted towards the bone 2 (rotation about a z-axis), twisted or swiveled about a y-axis, and cocked to one side or the other about an x-axis. Nevertheless, the first fixed clamp assembly 31 (e.g. the middle clamp assembly) has been tilted to a greater degree than the other two clamp assemblies while the second fixed clamp assembly 32 has been cocked more than the first two.

Referring back to FIG. 1, the joint mechanisms 36 are in turn coupled to the rail body 20 in either a fixed or movable manner with non-pivoting carriage portions 37, 38. For example, the rotatable portion 35 and the joint mechanism 36 of the movable clamp assembly 30 are supported by a movable carriage portion 37 which is configured to move or translate along the longitudinal axis 22 (also the z-axis) of the rail body 20. Meanwhile, the rotatable portions 35 and joint mechanisms 36 of the fixed clamp assemblies 31, 32 are secured with carriage portions 38 that are fixed against movement relative to the rail body 20.

Each clamp assembly 30, 31, 32 further includes one or more adjustable collar mechanisms 39 for holding and securing a bone screw 14, also known as a bone pin. The collar mechanisms 39 can pivot relative to the clamp assembly 30, 31, 32 in an unclamped state (e.g. when the clamp assembly is loose), and then become fixed and non-pivoting relative to the clamp assembly in a clamped state (e.g. when the clamp assembly is tightened).

During use, the bone screw 14 is inserted through a hole in the collar mechanism 39 to align the bone screw with a target location on the patient's bone 2. In one aspect, the collar mechanisms 39 of the clamp assemblies 30, 31, 32 can also function as a jig for aligning a drill bit to drill the bone 2 at the target location. The bone screw 14 can then be screwed into the bone 2 of the patient. The bone screw 14 can be rotated about its own longitudinal axis within the unclamped collar mechanism 39 as it is screwed into the bone 2, prior to tightening the clamp assembly.

In the illustrated embodiment, each collar mechanism 39 in each clamp assembly 30, 31, 32 can also be independently tilted up and down about a z-axis that is centered within the collar mechanism or angled side-to-side about a y-axis that is also centered within the collar mechanism.

Each clamp assembly 30, 31, 32 can include a top clamp nut 48 (FIG. 2). With a single mechanical action, the turning of the clamp nut 48 can provide for the simultaneous clamping of the rotatable portion 35 about the joint mechanism 36 and the clamping of the one or more collar mechanisms 39 about the bone screws 14. This can provide a distinct advantage to a user or surgeon for positioning and holding a clamp assembly 30, 31, 32 in one hand while turning the top clamp nut 48 with the other. However, it is considered that other devices and methods for activating the clamping function of the rotatable portions 35 about the joint mechanisms 36 and the clamping functions of the one or more collar mechanisms 39 about the bone screws 14 are also possible and considered to fall within the scope of the present disclosure, including those in which each clamping function is activated separately via separate clamping components.

The rail body 20 includes a reference or fixed end 21 and an actuator end 23, with a short side slot 25 formed proximate the fixed end and a long center slot 24 extending from near the side slot 25 towards the actuator end 23 (e.g. positioned between the short side slot 25 and the actuator end 23). As indicated above, the rotatable portion 35 and the joint mechanism 36 of the movable clamp assembly 30 can be coupled to the movable carriage portion 37, which is slidably installed within the center slot 24. In one aspect of the translation mechanism 34, the movable carriage portion 37 can include an internal screw thread (see FIG. 8) which is threadably engaged with the external screw threads of a lead bolt (also shown in FIG. 8) that is also positioned within the center slot 24, and which is concentric with the longitudinal axis 22 of the rail body 20. When the lead bolt is rotated within the rail body 20, the screw threads of the lead bolt push on the screw threads of the movable carriage portion 37, causing it to slide or translate in either direction along the longitudinal axis 22 in precision increments, depending on the direction of rotation. However, other types of translation mechanisms 24 for precisely moving the movable clamp assembly 30 relative to the rail body 20 are also possible and considered to fall within the scope of the present disclosure.

In some embodiment, the movable carriage portion 36 and lead bolt are similar to a previous design for an adjustable splint which was patented by the present inventor and disclosed in U.S. Pat. No. 7,507,240, which issued on Mar. 24, 2009, and which is incorporated herein by reference in its entirety.

The rotatable portion 35 and joint mechanism 36 of the first fixed clamp assembly 31 can be coupled to a carriage portion 38, which is installed within the side slot 25 formed near the fixed end 21 of the rail body 20. Once the carriage portion 38 of the fixed clamp assembly 31 is inserted into the side slot 25, it can be held in place and prevented from moving relative to the rail body 20 by the internal walls of the side slot, by a fastener, or by some other attachment means known to one of skill in the art.

The adjustable splint 10 of FIGS. 1-2 includes the optional second fixed clamp assembly 32 that also includes a rotatable portion 35 and a joint mechanism 37. The rotatable portion 35 and the joint mechanism 37 are coupled to another fixed carriage portion 38 that is installed into a side slot 29, similar to the side slot 25, but formed within a separable rail body extension 28. The rail body extension 28 with the second fixed clamp assembly 32 can then be attached to the fixed end 21 of the rail body 20 proximate the first fixed clamp assembly 31.

In some configurations of the adjustable splint the separable rail body extension 28 is not included and only the movable clamp assembly 30 and the first fixed clamp assembly 31 are coupled to the rail body 20. Further, although not shown, the adjustable splint can also include an optional second movable clamp assembly with a separable rail body extension coupled to the fixed end 21 of the rail body 20.

As illustrated in FIGS. 1-2, the two fixed clamp assemblies 31, 32 can be aligned angularly with one another (e.g. the slots can be on the same side of the adjustable splint 10). In other configurations, however, the rail body extension 28 supporting the second fixed clamp assembly 32 may be rotated about the longitudinal axis 22 of the rail body 20 so that two fixed clamp assemblies 31, 32 extend from opposite sides of the rail body, or at any angle there between. This feature allows the reference or fixed end 21 of the rail body 20 to be attached to the bone 2 of the patient with bone screws 14 entering from two or more substantially different directions, thereby providing a wider base for supporting the actuator end of the adjustable splint 10.

Figure 3:
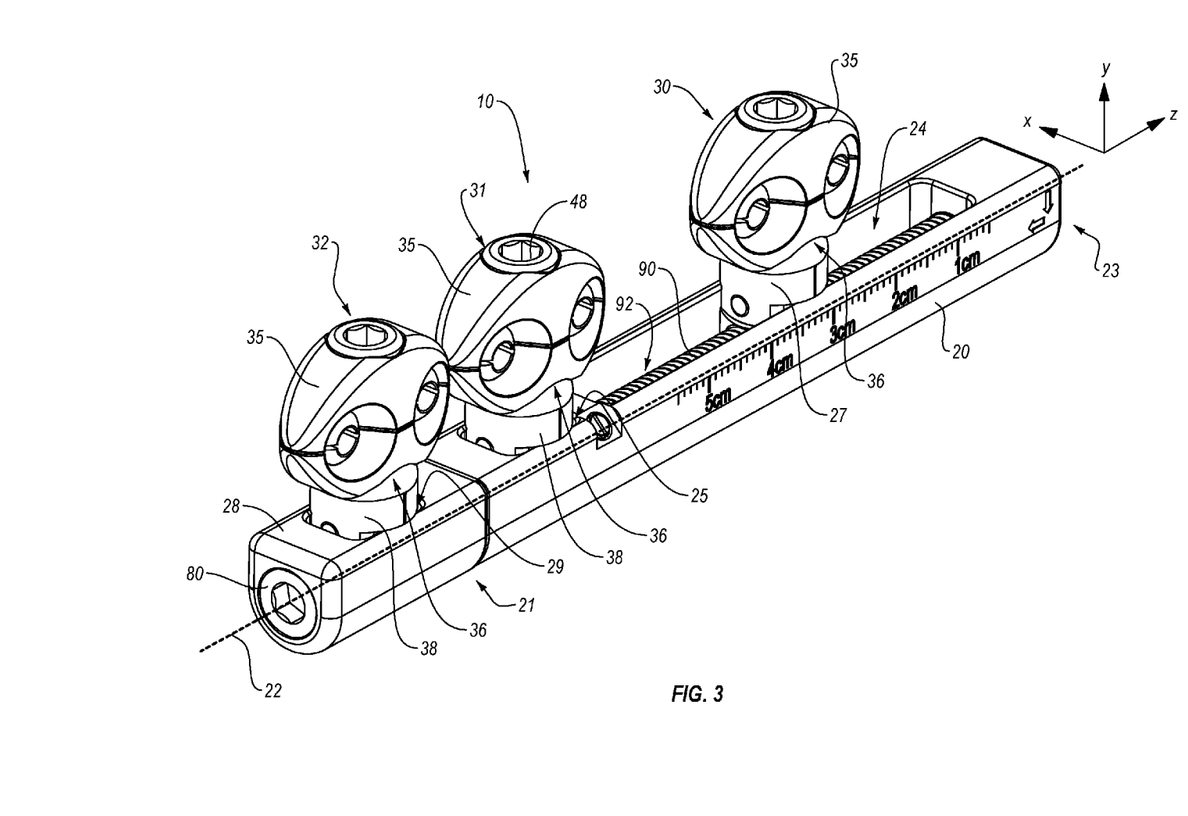
FIG. 3 is a perspective front view of the multi-axis adjustable splint of FIG. 1 in isolation.

In FIG. 3, the multi-axis adjustable splint 10 is shown in isolation without the bone of the patient and the bone pins which attach the adjustable splint to the patient's bone. As can be seen, the rail body 20 includes the center slot 24 for holding the movable clamp assembly 30 and the side slot 25 near the fixed end 21 for holding the first fixed clamp assembly 31. Also shown is the optional rail body extension 28 and the second fixed clamp assembly 32 attached to the rail body 20, with the two fixed clamp assemblies 31, 32 being positioned adjacent and parallel each other. In one aspect, the carriage portions 37, 38 which respectively attach each of the clamping assemblies 30, 31, 32 to the rail body 20 or to the rail body extension 28 can be substantially identical with each other so as to provide for a commonality and interchangeability of parts. However, each carriage assembly 37, 38 can be coupled to the rail body 20 or rail body extension 28 in a different way. For instance, each of the carriage portions 37, 38 can be sized to fit into the side slots 25, 29 and can include an internal screw thread. However, just the screw threads of the movable carriage portion 37 may be threadably engaged with the screw threads 92 of the lead bolt 90 (see FIG. 8), and the screw threads of the fixed carriage portion 38 of the first fixed clamping assembly 31 may be threadably engaged with the screw threads 86 of a fixed end screw 84 (see FIG. 7).

Figure 4:
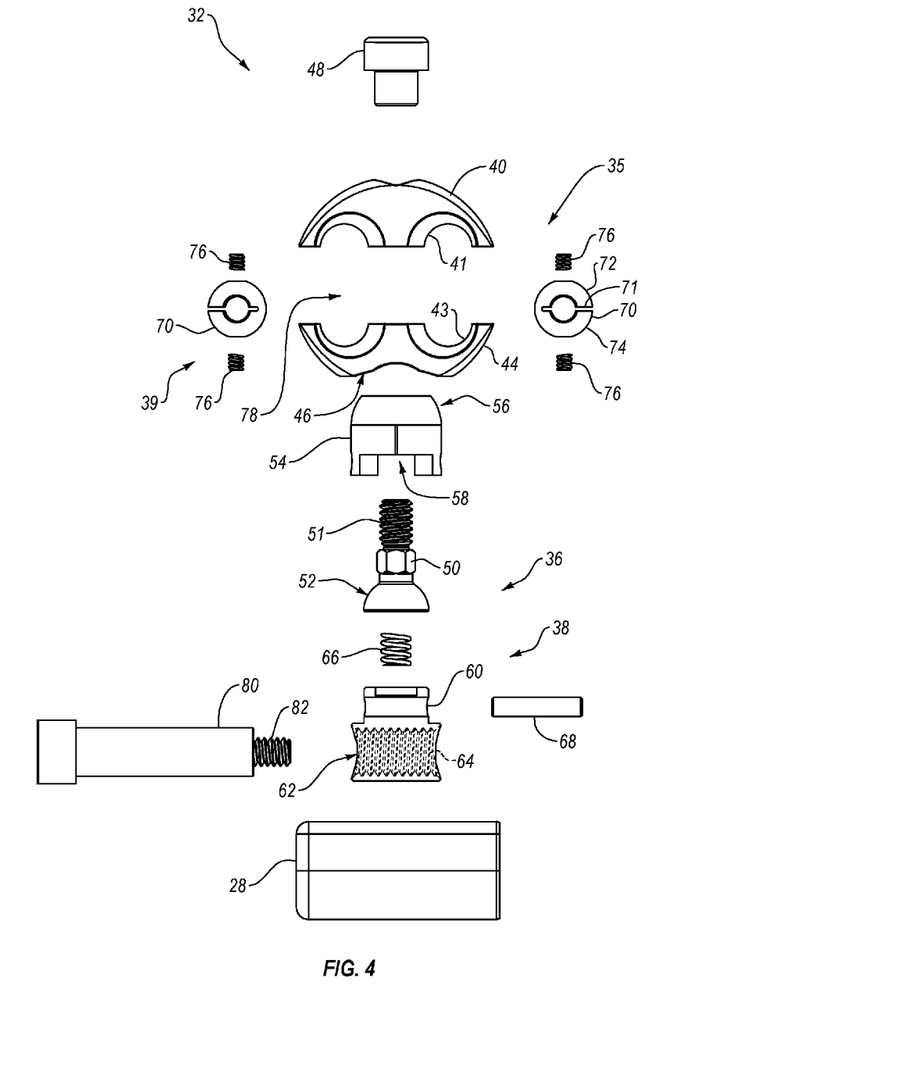
FIG. 4 is an exploded view of one of the clamp assemblies of the multi-axis adjustable splint of FIG. 1.

An exploded view of the second fixed clamp assembly 32 and the rail body extension 28 is shown in FIG. 4. Many if not most of the components of the second fixed clamp assembly 32 can be identical with the components of the movable clamp assembly 30 and the first fixed clamp assembly 31, with the differences being related to how the carriage portions 37, 38 of the clamp assemblies are coupled to the rail body 20 or rail body extension 28.

Beginning with the upper half of the drawing, the rotatable portion 35 of the clamp assembly 32 is that portion which is pivotable about the x-axis and z-axis, and rotatable about the y-axis of a pivot point centered within the joint mechanism 36, as is consistent with a ball-in-socket joint. In some implementations the rotatable portion 35 can pivot up to forty degrees from vertical in either direction and rotate three hundred and sixty degrees around the y-axis. In other implementations, however, the rotatable portion 35 may pivot less than forty degrees from vertical in either direction and rotate less than three hundred and sixty degrees around the y-axis.

The rotatable portion 35 includes a top clamp 40 and a top clamp nut 48 which installs within a top opening formed into the top clamp. The rotatable portion 35 also includes a bottom clamp 44 having a clamp bearing surface 46, and a ball joint bolt 50 having a bolt bearing surface 52. A threaded stud portion 51 of the ball joint bolt 50 is inserted upwardly through a vertically-oriented opening in the bottom clamp 44 and top clamp 48 for threaded engagement with the top clamp nut 48.

The rotatable portion 35 also includes the one or more collar mechanisms 39 which hold and secure the bone pins. The collar mechanisms 39 include spherical collars 70 installed into laterally-oriented sockets 78 formed by curved clamping surfaces 41, 43 formed into both the top clamp 40 and the bottom clamp 44, respectively. The shape of the spherical collars 70 can allow the spherical collars to be rotated into a variety of angular positions within their sockets 78 formed by the curved clamping surfaces 41, 43 prior to the tightening of the top clamp nut. The spherical collars 70 also include a compression slot 71 which separates the spherical collars into an upper half 72 and a lower half 74.

Spherical ball springs 76 are mounted into recesses formed within the curved clamping surfaces 41, 43 of the top clamp 40 and bottom clamp 44. The spherical ball springs 76 which are configured to apply a compressive preload force against the outsides of both the upper halves 72 and the lower halves 74 of the spherical collars 70, respectively. The compressive preload forces cause the upper halves 72 and the lower halves 74 to pinch together and to slightly close the compression slot 71 so that the spherical collar 70 can loosely (e.g. resistively, or with some resistance) hold the bone pins in place during positioning.

The non-rotatable portion or carriage portion 38 of the clamp assembly 32 includes a ball joint cap 54 having an outer bearing surface 56 which contacts the clamp bearing surface 46 of the bottom clamp 44 and an inner bearing surface 58 which contacts the bolt bearing surface 52 of the ball joint bolt 50. The ball joint cap 54 has a center aperture through which the threaded stud portion 51 of the ball joint bolt 50 is inserted. During assembly, the ball joint cap 54 is pressed down around the ball joint bolt 50 and attached to a nut actuator 60 with a press fit pin 68, with an actuator nut spring 66 being compressed between a recess in the top surface 61 of the nut actuator and a recess in the bottom surface 53 of the ball joint bolt 50. The actuator nut spring 66 operates to continuously push the bolt bearing surface 52 of the ball joint bolt 50 upwards against the inner bearing surface 58 of the call joint cap 54 to create a light friction contact within the joint mechanism 36 that can loosely or resistively hold the rotatable portion 35 in place during positioning.

After assembly of the ball joint cap 54 and the actuator nut 60 around the ball joint bolt 50 to form the carriage portion 38, the actuator nut 60 is inserted into the side slot 29 of the rail body extension 28 and held in place with one of a variety of mechanisms, including but not limited to an interference fit, an adhesive, or a fastener, etc. This prevents the actuator nut 60 from moving laterally or from sliding back out of the side slot 29. An extension shoulder bolt 80 can then be inserted through the threaded hole 62 in the actuator nut 60. The extension shoulder bolt 80 can also include a smaller-diameter threaded portion 82 which is used to couple the rail body extension 28 to the fixed end of the rail body (see FIG. 3).

Figure 5:
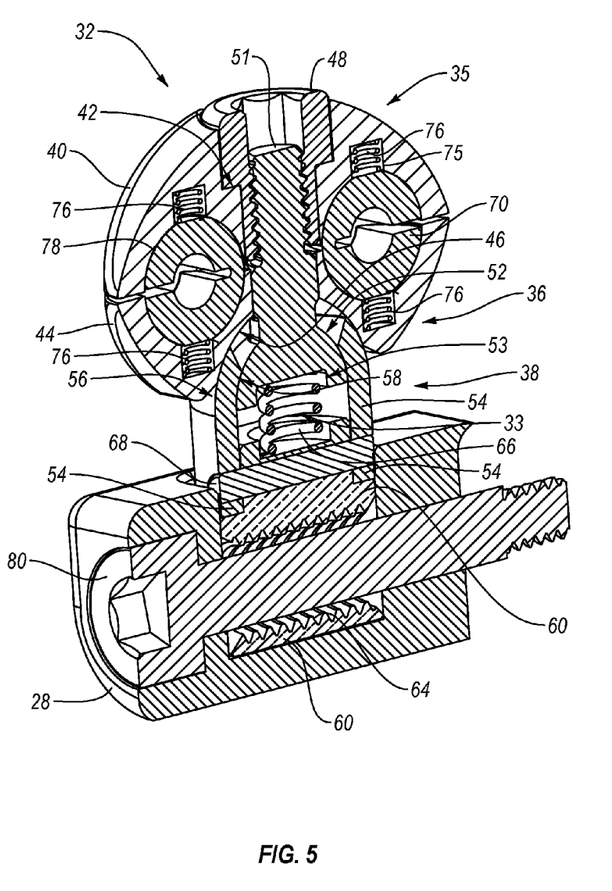
FIG. 5 is a perspective cross-sectional front view of the clamp assembly of FIG. 4.

FIG. 5 is a perspective cross-sectional front view of the assembled second fixed clamp assembly 32 which provides additional detail has to how each component of the clamp assembly fits with the other components. In the representative embodiment, the joint mechanism 36, which provides the rotation of the rotatable portion 35 about the pivot point 33, is formed primarily by the interrelationship between the ball joint bolt 50, the ball joint cap 54, and the clamp surface 46 of the bottom clamp 44. This interrelationship is in turn affected by compressive loads provided by the actuator nut spring 68 from below and the top clamp 40 and the top clamp nut 48 from above.

During the assembly of the rotatable portion 35 of the clamp assembly 32, for instance, the top clamp nut 48 is threaded around the threaded stud portion 51 of the ball joint bolt 50 and tightened at least finger-tight against the interior shoulder 42 of the top clamp 40. This may create only a loose contact between the clamp bearing surface 46 of the lower clamp 44 and the outer bearing surface 56 of the ball joint cap 54, which will not hinder movement of the rotatable portion 35. However, the ball joint bolt 50 will be pressed upwards by the compressed actuator nut spring 68 so that the bolt bearing surface 52 contacts the inner bearing surface 58 of the ball joint cap 54 with enough normal force to produce the light friction contact described above. The friction contact at the lower interface can be sufficient to hold the rotatable portion 35 in position against the force of gravity or similar small loads, but will still allow the rotatable portion to be moved about the x-, y- or z-axis when manipulated by the user or surgeon.

Once the rotatable portion 35 has been rotated and/or angled to its desired position, the top clamp nut 48 can be tightened further onto the threaded stud portion 51 of the ball joint bolt 50, which action applies additional loading against the interior shoulder 42 of the top clamp 40. This causes the top clamp 40, which may not directly contact the bottom clamp, to bear against the spherical collar 70. The spherical collar 70 in turn transfers the load to the bottom clamp 44, which then increases the pressure between the clamp bearing surface 46 and the outer bearing surface 56 of the ball joint cap 54. Simultaneously, the ball joint 50 is placed in tension as the bolt bearing surface 52 is pulled upwards with greater pressure against the inner bearing surface 58. As a result, the upper dome of the ball joint cap 54 is compressed between the bolt bearing surface 52 and clamp bearing surface 46 to create a strong friction contact that is sufficient to resist additional outside forces.

Figure 9:
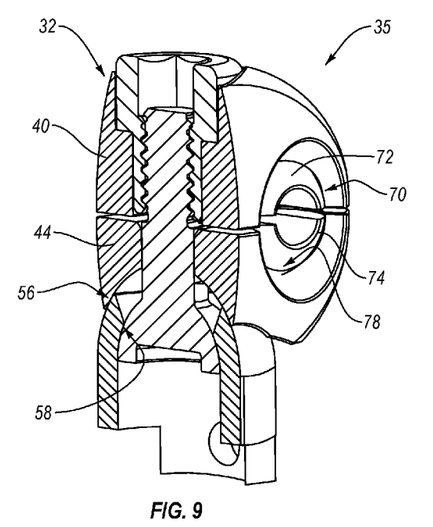
FIG. 9 is a close-up perspective cross-sectional side view of one of the clamp assemblies of the multi-axis adjustable splint of FIG. 1.
Figure 10:
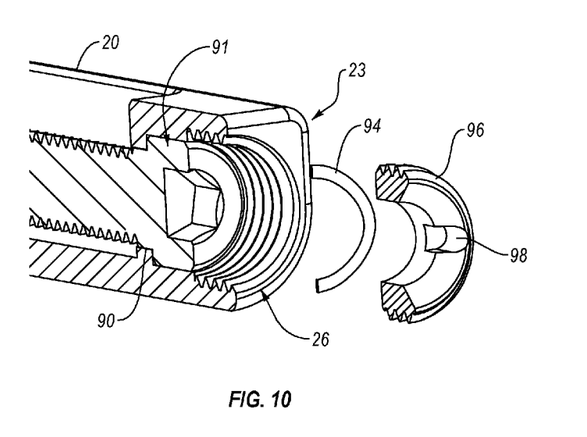
FIG. 10 is a close-up perspective cross-sectional front view of one end of the rail body of the multi-axis adjustable splint of FIG. 1.

Referring briefly to FIG. 9, simultaneous with the compression between the inner 58 and outer 56 bearing surfaces of the ball joint cap 54 to restrain motion of the rotatable portion 35, the transfer of forces between the top clamp 40 and the bottom clamp 44 also causes the upper halves 72 and the lower halves 74 of the spherical collars 70 to pinch together and close more tightly around the bone screws (see FIGS. 1 & 2). This action operates both to secure the spherical collars 70 within their respective sockets 78 to prevent additional angular movement of the bone screws, as well as to secure the clamp assembly 32, and hence the entire adjustable splint, to the bone screws which have been attached to the patient's bone.

Figure 6:
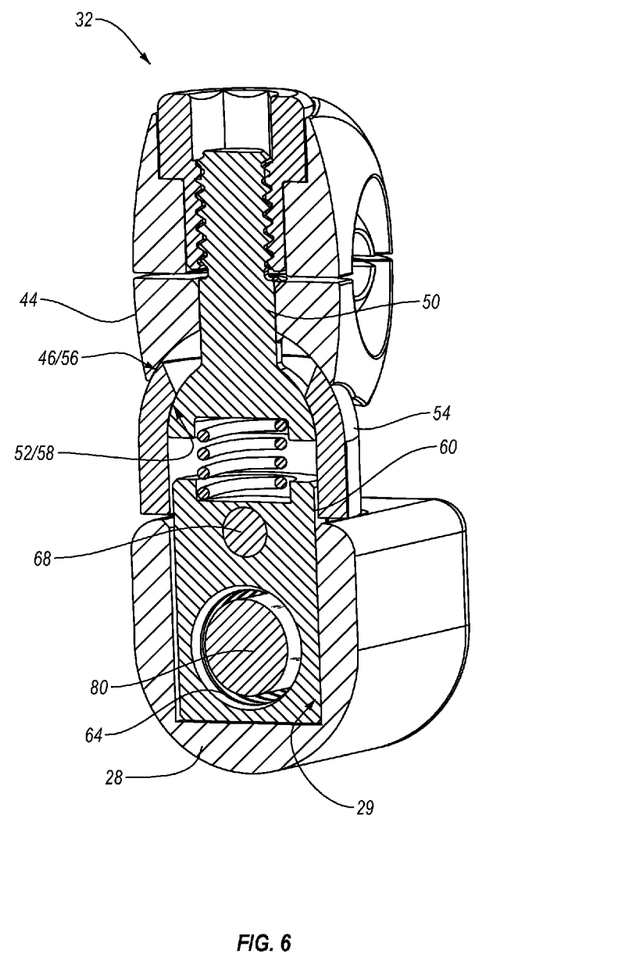
FIG. 6 is a perspective cross-sectional side view of the clamp assembly of FIG. 4.

Illustrated in FIG. 6 is a perspective cross-sectional side view of the clamp assembly 32 which provides another angle of the interface 52/58 between the ball joint bolt 50 and the ball joint cap 54 and the interface 46/56 between the ball joint cap 54 and the bottom clamp 44. Also shown in FIG. 6 is a clearance between the non-threaded surface of the extension shoulder bolt 80 and the internal threads 64 of the actuator nut 60. In this configuration the actuator nut 60 can be coupled directly to the interior walls of the slide slot 29, either with an adhesive or with a press fit, etc., while the extension shoulder bolt 80 is principally used to attach the rail body extension 28 to the rail body.

Figure 7:
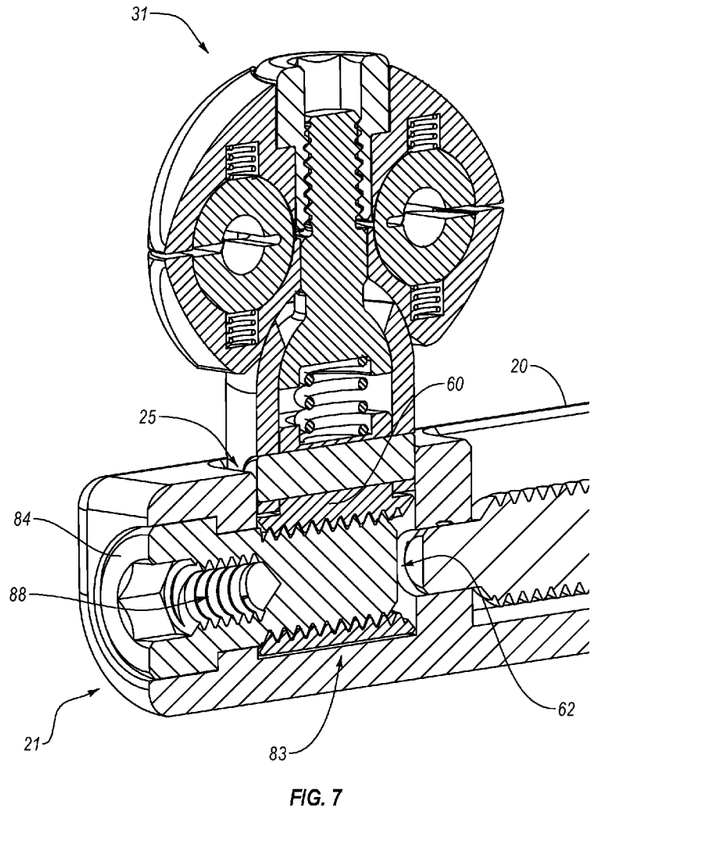
FIG. 7 is a perspective cross-sectional front view of another clamp assembly of the multi-axis adjustable splint of FIG. 1.

FIG. 7 is a perspective cross-sectional front view of the first fixed clamp assembly 31 installed into the side slot 25 of the rail body 20 near the reference or fixed end 21 of the rail body. As described above, the first fixed clamp assembly 31 can be substantially identical with the second fixed clamp assembly except for the fixed end screw 84 having a threaded portion 86 which is threaded into the threaded bore 62 of the first fixed clamp assembly's actuator nut 60. The fixed end screw 84 can further included a threaded counterbore 88 for receiving the threaded portion of the extension shoulder bolt.

Figure 8:
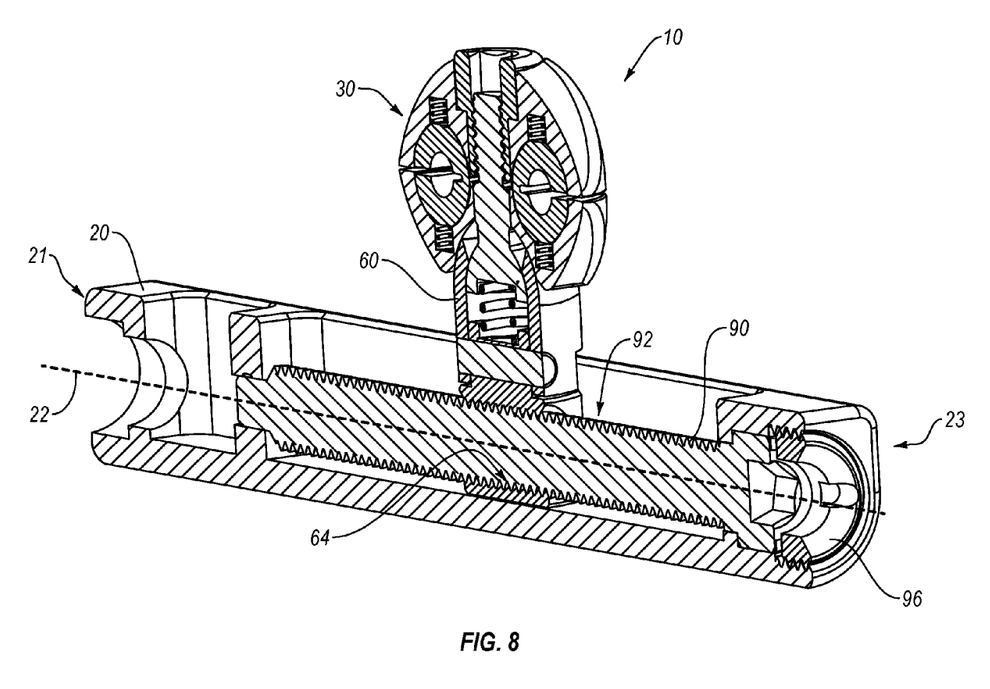
FIG. 8 is a perspective cross-sectional front view of another clamp assembly and the rail body of the multi-axis adjustable splint of FIG. 1.

Illustrated in FIG. 8 is a perspective cross-sectional front view of the movable clamp assembly 30 and the rail body 20 of the multi-axis adjustable splint 10, in which the movable clamp assembly can be substantially identical with one or more fixed clamp assemblies except for the internal screw threads 64 of its actuator nut 60 being threadably engaged with the external screw 92 threads of the lead bolt 90. When the lead bolt 90 is rotated within the rail body 20, the screw threads 92 of the lead bolt push against the screw threads 64 of the movable clamp assembly's actuator nut 60, causing it to slide or translate in either direction along the longitudinal axis 22.

Once the movable clamp assembly 30 has been moved to its desired position along the longitudinal axis 22 of the rail body 20, the lead bolt 90 can be secured against further rotation with the installation of an actuator screw cap 96 which locks the angular position of the lead bolt. As shown with more detail in FIG. 10, for instance, a wave spring 94 can be can be inserted into the actuator opening 26 at the actuator end 23 of the rail body 20. The wave spring 94 is followed by the actuator screw cap 96 which is threaded into the actuator opening 26 until the wave spring is compressed between the head 91 of the lead bolt 90 and the inside face of the actuator screw cap. This compression of the wave spring 94 can create a self-locking friction fit which prevents rotation of the lead bolt. If desired, the actuator screw cap 96 can also include depressions 98 which allow for the deformation of the threads of the actuator screw cap into the threads formed into the actuator opening 26, further securing the actuator screw cap, wave spring 94 and lead bolt 90 against inadvertent rotation.

In the above description, certain terms may be used such as "up," "down," "upper," "lower," "horizontal," "vertical," "left," "right," and the like. These terms are used, where applicable, to provide some clarity of description when dealing with relative relationships. But, these terms are not intended to imply absolute relationships, positions, and/or orientations. For example, with respect to an object, an "upper" surface can become a "lower" surface simply by turning the object over. Nevertheless, it is still the same object. Further, the terms "including," "comprising," "having," and variations thereof mean "including but not limited to" unless expressly specified otherwise.

Additionally, instances in this specification where one element is "coupled" to another element can include direct and indirect coupling. Direct coupling can be defined as one element coupled to and in some contact with another element. Indirect coupling can be defined as coupling between two elements not in direct contact with each other, but having one or more additional elements between the coupled elements. Further, as used herein, securing one element to another element can include direct securing and indirect securing. Additionally, as used herein, "adjacent" does not necessarily denote contact. For example, one element can be adjacent another element without being in contact with that element.

As used herein, the phrase "at least one of", when used with a list of items, means different combinations of one or more of the listed items may be used and only one of the items in the list may be needed. The item may be a particular object, thing, or category. In other words, "at least one of" means any combination of items or number of items may be used from the list, but not all of the items in the list may be required. For example, "at least one of item A, item B, and item C" may mean item A; item A and item B; item B; item A, item B, and item C; or item B and item C. In some cases, "at least one of item A, item B, and item C" may mean, for example, without limitation, two of item A, one of item B, and ten of item C; four of item B and seven of item C; or some other suitable combination.

The subject matter of the present disclosure may be embodied in other specific forms without departing from its spirit or essential characteristics. The described embodiments are to be considered in all respects only as illustrative and not restrictive. The scope of the disclosure is, therefore, indicated by the appended claims rather than by the foregoing description. All changes which come within the meaning and range of equivalency of the claims are to be embraced within their scope.

What is claimed is:

1. An adjustable splint for treating the fracture of bones, comprising:
    a rail body having a longitudinal axis;
    a fixed clamp assembly coupled to the rail body for securing at least one first bone screw in a first desired orientation, the fixed clamp assembly being translationally fixed relative to the rail body; and
    a movable clamp assembly movably coupled to the rail body for securing at least one second bone screw in a second desired orientation, the movable clamp assembly being translatable along the longitudinal axis of the rail body;
    wherein the fixed clamp assembly and the movable clamp assembly are each independently adjustable about three axes of rotation relative to the rail body;
    wherein the fixed clamp assembly and the movable clamp assembly each comprises a carriage portion coupled to the rail body, a joint mechanism connected to the carriage portion, and a rotatable portion that is pivotally engaged with the joint mechanism;
    wherein each rotatable portion comprises a socket, the adjustable splint further comprising a spherical collar rotatably supported within the socket and configured to receive and hold a respective one of the at least one first bone screw and the at least one second bone screw, wherein the spherical collar is independently rotatably adjustable about three axes of rotation relative to the rotatable portion;
    wherein a single clamp nut engaged with the clamp assembly is tightenable to secure both the rotatable position of the spherical collar within the socket and the rotatable position of the rotatable portion about the joint mechanism;
    wherein the rail body comprises a lead bolt extending longitudinally within the rail body that is threadably engaged with the movable clamp assembly, wherein rotation of the lead bolt within the rail body causes the movable clamp assembly to move along the longitudinal axis of the rail body; and
    wherein the lead bolt comprises an actuator screw cap that rotatably locks the position of the lead bolt in order to secure the translational position of the movable clamp assembly.

2. The adjustable splint of claim 1, wherein the rotatable portion comprises a top clamp member and a bottom clamp member that clamp around the first or second bone screws.

3. The adjustable splint of claim 1, wherein the rotatable portion comprises two spherical collars rotatably supported within two sockets, wherein the spherical collars are independently adjustable relative to each other.

4. The adjustable splint of claim 1, wherein the joint mechanism comprises a ball-joint bolt assembly that engages the rotatable portion.

5. The adjustable splint of claim 1, further comprising an additional fixed clamp assembly.

6. The adjustable splint of claim 1, further comprising an additional movable clamp assembly.

7. An adjustable splint for treating the fracture of bones, comprising:
    a rail body comprising a lead bolt extending longitudinally within the rail body;
    a fixed clamp assembly comprising a carriage portion translational fixed to the rail body, a joint mechanism connected to the carriage portion, and a rotatable portion that is pivotally engaged to the joint mechanism, wherein the rotatable portion comprises a top clamp member and a bottom clamp member that clamp around a first bone screw to secure the first bone screw in a first desired orientation; and
    a movable clamp assembly comprising a carriage portion mounted to the lead bolt so as to be movable along the length of the rail body, a joint mechanism connected to the carriage portion, and a rotatable portion that is pivotally engaged to the joint mechanism, wherein the rotatable portion comprises a top clamp member and a bottom clamp member that clamp around a second bone screw to secure the second bone screw in a second desired orientation;
    wherein the fixed clamp assembly and the movable clamp assembly are each independently adjustable about three axes of rotation relative to the rail body;
    wherein the top clamp member and the bottom clamp member of the rotatable portion of each of the fixed clamp assembly and the movable clamp assembly collectively define a socket, the adjustable splint further comprising a spherical collar rotatably supported within the socket and configured to receive and hold a respective one of the first bone screw and the second bone screw, wherein the spherical collar is independently rotatably adjustable relative to the rotatable portion;
    wherein the rotatable portion of each of the fixed clamp assembly and the movable clamp assembly further comprises spherical ball springs configured to apply a compressive preload force against both upper and lower halves of each spherical collar to bias the upper and lower halves together.

8. The adjustable splint of claim 7, wherein the fixed clamp assembly and the movable clamp assembly each comprise a single clamp nut that is tightenable to secure both the position of the spherical collar within the socket and the position of the rotatable portion about the joint mechanism.

9. The adjustable splint of claim 7, wherein each rotatable portion comprises two spherical collars rotatably supported within two sockets, wherein the spherical collars are independently adjustable relative to each other.

10. The adjustable splint of claim 7, wherein the rail body is a first rail body and the adjustable splint further comprises a second rail body coupled to the first rail body, and wherein at least one of a second fixed clamp assembly and a second movable clamp assembly is coupled to the second rail body.

11. An adjustable drilling jig for guiding drill bits for treating the fracture of bones, comprising:
- a rail body having a longitudinal axis;
- a fixed clamp assembly coupled to the rail body for securing at least one first drill jig in a first desired orientation, the fixed clamp assembly being translationally fixed relative to the rail body; and
- a movable clamp assembly movably coupled to the rail body for securing at least one drill jig in a second desired orientation, the movable clamp assembly being translatable along the longitudinal axis of the rail body;
- wherein the fixed clamp assembly and the movable clamp assembly are each independently adjustable about three axes of rotation relative to the rail body;
- wherein the fixed clamp assembly and the movable clamp assembly each comprises a carriage portion coupled to the rail body, a joint mechanism connected to the carriage portion, and a rotatable portion that is pivotally engaged with the joint mechanism;
- wherein each rotatable portion comprises a socket, the adjustable splint further comprising a spherical collar rotatably supported within the socket and configured to receive and hold a respective one of the at least one first drill jig and the at least one second drill jig, wherein the spherical collar is independently rotatably adjustable about three axes of rotation relative to the rotatable portion; and
- wherein a single clamp nut engaged with the clamp assembly is tightenable to secure both the rotatable position of the spherical collar within the socket and the rotatable position of the rotatable portion about the joint mechanism; and
- wherein the rotatable portion of each of the fixed clamp assembly and the movable clamp assembly further comprises spherical ball springs configured to apply a compressive preload force against both upper and lower halves of each spherical collar to bias the upper and lower halves together.

* * * * *